United States Patent [19]

Oyague et al.

[11] Patent Number: 6,080,894
[45] Date of Patent: Jun. 27, 2000

[54] PROPYLENE OXIDE AND STYRENE MONOMER CO-PRODUCTION PROCEDURE

[75] Inventors: Juan Antonio Delgado Oyague; Pilar De Frutos Escrig, both of Madrid; Ignacio Vic Fernandez, Las Matas, all of Spain

[73] Assignee: Repsol Quimica S.A., Madrid, Spain

[21] Appl. No.: 09/040,016

[22] Filed: Mar. 17, 1998

[51] Int. Cl.[7] .......................... C07C 27/10; C07C 29/10; C07C 35/00; C07C 7/00
[52] U.S. Cl. .......................... 568/700; 549/523; 549/525; 549/529; 585/435; 585/437; 585/469; 585/805
[58] Field of Search ............................ 585/469, 435, 585/805, 437; 549/523, 525, 529; 568/700

[56] References Cited

U.S. PATENT DOCUMENTS 5,210,354  5/1993  Dubner et al. ........................ 585/469
5,276,235  1/1994  Dubner ................................ 585/469

*Primary Examiner*—Gary L. Kunz
*Assistant Examiner*—Everett White
*Attorney, Agent, or Firm*—Marshall, O'Toole, Gerstein, Murray & Borun

[57] ABSTRACT

The propylene oxide and styrene co-production process generates a heavy residue byproduct containing metals, mainly sodium, which previously was adequate for use only as low quality fuel. According to the invention, the heavy residue is dehydrated in the presence of a strong inorganic acid at temperatures of 150–250° C. and pressures below the atmospheric pressure to yield styrene and recover 2-phenylethanol, a compound used in the perfume industry, and a heavy residue substantially free of metals that may be used as fuel.

8 Claims, No Drawings

PROPYLENE OXIDE AND STYRENE MONOMER CO-PRODUCTION PROCEDURE

DESCRIPTION OF THE PRIOR ART

U.S. Pat. No. 5,210,354 refers to an improved propylene oxide and styrene co-production procedure. The improvement consists in revaluating heavy sodium-containing residual currents, obtained as a byproduct. According to this procedure, the heavy sodium-containing residue is mixed with an aqueous acid, preferably sulfuric acid, in relatively mild conditions, e.g. 20–100° C., preferably 40–90° C. The resulting mixture is separated in immiscible phases, one aqueous phase containing sodium and another organic phase having a limited sodium content. To the organic phase a compatible acid catalyst is added, such as p-toluenesulfonic acid, and the resulting mixture is cracked at high temperature to form 1-phenylethanol and styrene monomer, which products may be separated from the remaining heavy compounds through distillation. Temperatures of 70 to 300° C., preferably 120 to 220° C., and pressures below the atmospheric pressure, such as 100–400 mm.Hg, appropriate for vaporizing the light compounds, are used for the cracking. The cracking products, 1-phenylethanol and styrene, entail an increased performance of the styrene in the course of the process in view that 1-phenylethanol is a styrene precursor. Furthermore, the heavy cracking products are useful as low sodium content fuels. In a most preferred variant of the process, after the acid treatment the organic phase is submitted to vacuum evaporation in a film evaporator designed to separate approximately 40% by weight of a fraction of volatile compounds. This top fraction may be taken directly to the dehydration section of commercial propylene/styrene oxide co-production processes where certain components of the light header fraction are transformed into styrene under the conditions normally applied to 1-phenylethanol dehydration. The heavy film evaporator residues are used as revalued fuel on account of their low sodium content.

The acid is used in sufficient quantity to react with all the sodium present in the heavy residue. In the event that sulfuric acid is used, a sufficient amount of acid is applied to form sodium sulfate, i.e. less than 0,5 moles of sulfuric acid for each atom gram of sodium and preferably less than 1 mole of sulfuric acid for each atom gram of sodium to form sodium bisulfate.

U.S. Pat. No. 5,276,235 refers to an improvement to the procedure described in the preceding patent. A critical aspect in this innovation lies in that the acid used for reacting with the sodium present in the heavy residue is applied in a mole concentration corresponding to the salt concentration in the aqueous solution produced above the solvency limit. Thus, the salt generated by the reaction forms a suspension in the phase mixture which in turn maximizes density differences between the phases, facilitates separation and reduces organic matter contamination in the aqueous phase.

The process described in the previous patents presents a disadvantage in that it produces relatively low styrene yields and generates high salt content aqueous currents contaminated by organic compounds which require depuration, for example via biological degrading. In addition, phase separation is problematic.

DESCRIPTION OF THE INVENTION

The present invention refers to an improved propylene oxide and styrene monomer co-production procedure. The improvement consists in obtaining additional amounts of styrene and recovering 2-phenylethanol from a heavy residual current containing metals, mainly sodium, obtained in the form of a process byproduct. According to the procedure that is the object of the invention, styrene yields are greater than those from prior art procedures; a fraction with a high 2-phenylethanol content, a compound used in the perfume industry, is simultaneously obtained; no highly metal salt and organic compound contaminated waters are generated, and a non-volatile, substantially metal-free residue is obtained that may serve as an appropriate fuel.

The known propylene oxide and styrene co-production process is described, for instance, in Spanish patents No. 314,229, 314,231, 307,877, 320,168, 323,754, 331,818, 334,098, 335,098, 343,579 and 365,624. In a first stage, ethyl benzene is made to react at high temperature with molecular oxygen in order to produce ethyl benzene hydroperoxide. The ethyl benzene hydroperoxide reacts with propylene to form propylene oxide and 1-phenylethanol. The mixture resulting from the epoxydizing reaction is normally submitted to alkaline rinsing and to a series of distillations designed to separate the various components: propylene oxide, non-reacted ethyl benzene and 1-phenylethanol, leaving a heavy residue with a low content of sodium and other metals. The 1-phenylethanol current is dehydrated through known procedures, such as the one using p-toluenesulfonic acid as a catalyst for producing styrene monomer, as described, for example, in Japanese patent Kokai 8019247.

According to the present invention, the low-value sodium-containing heavy residue may be used directly, without previous metal removal, particularly sodium, as raw material for the production of styrene—a fraction with a relatively high 2-phenylethanol content, which is a compound used in the perfume industry—, and a heavy residue with a low sodium content, used as fuel.

According to the invention, the heavy residue containing sodium and other metals is dehydrated in the presence of a strong inorganic acid acting as a catalyst, at temperatures between approximately 150 and 250° C. and pressures below the atmospheric pressure, preferably 50–400 mm.Hg, simultaneously vaporizing the light compounds, mainly styrene formed in the reaction and 2-phenylethanol; this organic distillation, representing approximately 30 to 50% by weight of the heavy residue, is then fractionated by known methods, such as distillation, in order to recover pure styrene and a fraction containing relatively high amounts of 2-phenylethanol. This fraction can be used as a raw material for producing perfumery-degree 2-phenylethanol via known procedures. The residue of the non-volatile reaction is composed of heavy organic products, sodium salts and other inorganic acid metals and traces of the excess mineral inorganic acid. The metal salts may be easily separated from the organic products, e.g. by filtering, yielding a non-volatile organic residue practically exempt of sodium and other metals that is appropriate for fuel purposes.

Evidently, and according to the invention, the heavy residues from which most of the sodium and other metals have been removed by known procedures, such as treatment with aqueous acids and subsequent separation in phases, may be used as a raw material. However, this practice is normally not advisable in the context of the present invention because of the inconveniences associated to the type of treatment in question.

The strong inorganic acid used in treating the heavy residue containing sodium and other metals is preferably sulfuric acid. Other inorganic acids that may be used within the scope of the present invention include phosphoric, pyrophosphoric, polyphosphoric and fluorophosphoric acids, in addition to $V_2O_5$ solutions in polyphosphoric acids, etc. Mixtures of the above inorganic acids may also be used.

The strong inorganic acid must be used in an amount in excess of the stoichiometrical amount in order to allow it to react with all the sodium and other metals present in the heavy residue. It must be used in an amount above 1 acid equivalent per atom gram of sodium and other metals. The excess above the stoichiometrical amount is not critical. Normally, it is preferable to use the strong acid in a quantity high enough to provide, after reacting with the sodium and other metals, a free acid concentration in the reaction medium in the order of 0.001 to 1% by weight. With the use of smaller quantities, reaction is relatively slow; on the other hand, the use of larger quantities provides no additional advantage.

EXAMPLE 1

The dehydration reaction of the heavy residue took place in a 50-liter glass reactor fitted with stirring means and connected at its upper portion to a water-cooled condenser. Vacuum was obtained from a water pump providing a constant pressure of 220 mm.Hg. 30 kg of heavy residues (1.0% by weight of sodium) and 0.7 kg of 96% sulfuric acid were initially added. Vacuum was applied at 220 mm.Hg, and the mixture was slowly heated to 220° C. Subsequently, continuous feeding of the heavy residue (1.0% by weight of sodium) and the 96% sulfuric acid was initiated in flow volumes of 10 kg/h and 0.23 kg/h, respectively, a non-volatile residue containing sodium sulfates and other metals being simultaneously extracted from the bottom in an average flow of 5.68 kg/h, and an organic distillate at an average flow of 4.32 kg/h being extracted from the top, comprising 44.4% styrene, 12.9% 2-phenylethanol, 1.8% acetophenone and 0.7% 1-phenylethanol, the balance containing mainly water and oxygenated compounds such as propylene oxide condensation products, ethers, etc.

With the practical application of this invention, styrene production is increased in 2.09%; this, in a commercial production facility capable of producing 500.000 tons of styrene per year, represents an added value of 888 million pesetas at current styrene prices.

EXAMPLE 2

The reaction was performed in an installation similar to the one described in Example 1, save for the use of a 1-liter capacity reactor. Reaction temperature was 193° C., pressure was 140 mm.Hg. 302 gr/h of heavy residues (1.0% by weight of sodium) and 9.0 gr/h of 75% sulfuric acid were continuously added to the reactor. 127.3 gr/h (42.2% by weight of the heavy residues fed) of organic distillate and 18.5 gr/h water were obtained from the top of the reactor, and a current of 165.2 gr/h of non-volatile residues (54.7% by weight of the heavy residues fed) was obtained from the bottom of the reactor. The organic distillates were composed of 66.2% styrene, 22.0% 2-phenylethanol, 2.2% acetophenone, 1.8% 1-phenylethanol and 7.8% by weight of different oxygenated products, including propylene oxide condensation products, ether, etc.

Comparative Example 2

Example 2 was repeated exactly under the same conditions save for the replacement of the strong inorganic acid flow according to the invention, namely 9.0 gr/h, by a 21.9 gr/h flow of p-toluenesulphonic acid, an organic acid normally recommended for 1-phenylethanol dehydration. A yield was obtained amounting to 49.8% by weight in respect to the amount of heavy residue being fed, the composition of which was: 0.6% styrene, 25% 2-phenylethanol, 2.2% acetophenone, 18.0% 1-phenylethanol and 54.2% by weight of different oxygenated products, including propylene oxide condensation products, ether, etc.

This example illustrates the advantages of the heavy residue treatment according to the invention.

EXAMPLE 3

The organic distillate current obtained in Example 1 was fractionated by distillation to recover 99.3%-rich styrene and a current containing 24.7% 2-phenylethanol usable to advantage as raw material for the recovery of 2-phenylethanol, perfumery degree, according to known procedures.

EXAMPLE 4

The non-volatile residue containing sodium sulfates and other metals obtained in Example 1 were filtered at 80° C. through a No. 4 porous glass plate, yielding a filtered matter containing <0.1% sulfate ash usable as revalued fuel.

The above examples illustrate the invention and impose no limitation on it.

We claim,:

1. A process for the co-production of propylene oxide and styrene monomer comprising the steps of oxidizing ethylbenzene with molecular oxygen to produce ethylbenzene hydroperoxide; reacting said ethylbenzene hydroperoxide with propylene to form propylene oxide and 1-phenyl ethanol; separately recovering unreacted propylene, propylene oxide, and 1-phenyl ethanol by distillation to leave a heavy residue containing sodium and oxygen-containing organic materials formed in the process; and dehydrating the 1-phenyl ethanol to styrene, the improvement comprising the steps of:

(a) admixing the heavy residue with a strong inorganic acid as a catalyst, at a temperature in the range of 150° C. to 250° C. and a pressure below atmospheric pressure, the strong inorganic acid being present in an amount exceeding the stoichiometric amount with respect to the sodium contained in the residue, to thereby obtain a stream of vaporized light compounds, said stream comprising styrene and 2-phenyl ethanol, and a non-volatile residue containing sodium and heavy organic compounds; and (b) fractionating the stream of vaporized light compounds to recover pure styrene and a fraction containing 2-phenyl ethanol.

2. The process of claim 1 wherein the strong inorganic acid is sulfuric acid.

3. The process of claim 1 comprising the step of adding the strong inorganic acid in at least an amount sufficient to react with all of the sodium in the heavy residue.

4. The process of claim 3 comprising the step of adding the strong inorganic acid in at least an amount above one acid equivalent per atom gram of sodium in the heavy residue.

5. The process of claim 1 comprising the step of adding the strong inorganic acid in an amount sufficient to provide, after reacting with the sodium in the heavy residue, a free acid concentration in the reaction medium between 0.001 wt. % and 1 wt. %.

6. The process of claim 1 wherein the pressure in step (a) is 50 mm Hg to 400 mm Hg, absolute.

7. The process of claim 1 comprising the step of fractionating the stream of vaporized light compounds comprising styrene and 2-phenyl ethanol by distillation to recover pure styrene and a fraction containing 2-phenyl ethanol.

8. The process of claim 1 comprising the step of filtering the non-volatile residue containing sodium and heavy organic compounds to separate sodium salts and to obtain a non-volatile organic residue having a reduced sodium content.

* * * * *